United States Patent [19]
Venkitaraman et al.

[11] Patent Number: 5,871,762
[45] Date of Patent: Feb. 16, 1999

[54] COSMETIC APPLICATORS WHICH CONTAIN STABLE OIL-IN-WATER EMULSIONS

[75] Inventors: Anand Rudra Venkitaraman, Cincinnati, Ohio; Michael Thomas Dodd, Edgewood, Ky.; David John Pung, Maineville, Ohio

[73] Assignee: The Procter & Gamble Company, Cincinnati, Ohio

[21] Appl. No.: 727,807

[22] Filed: Oct. 7, 1996

[51] Int. Cl.[6] ................................................. A01N 25/34
[52] U.S. Cl. ........................ 424/402; 424/401; 514/937
[58] Field of Search .................. 424/402, 401; 514/937

[56] References Cited

U.S. PATENT DOCUMENTS

| | | | |
|---|---|---|---|
| 3,965,518 | 6/1976 | Muoio | 15/104.93 |
| 4,559,157 | 12/1985 | Smith et al. | 252/90 |
| 4,732,797 | 3/1988 | Johnson | 428/74 |
| 4,781,974 | 11/1988 | Bouchette et al. | 428/288 |
| 4,788,060 | 11/1988 | Endicott et al. | 424/443 |
| 4,844,891 | 7/1989 | Rosen et al. | 424/76.4 |
| 4,853,281 | 8/1989 | Win et al. | 428/286 |
| 4,904,524 | 2/1990 | Yoh | 428/311.3 |
| 5,043,155 | 8/1991 | Puchalski et al. | 424/78 |
| 5,049,440 | 9/1991 | Bornhoeft, III et al. | 428/288 |
| 5,300,286 | 4/1994 | Gee | 424/78.03 |
| 5,362,488 | 11/1994 | Sibley et al. | 424/78.05 |
| 5,512,199 | 4/1996 | Khan | 252/106 |

FOREIGN PATENT DOCUMENTS

| | | |
|---|---|---|
| 0197485 | 10/1986 | European Pat. Off. . |
| 0564307 A1 | 10/1993 | European Pat. Off. . |
| 613675 | 9/1994 | European Pat. Off. . |
| 0 759291 A1 | 2/1997 | European Pat. Off. . |
| 3924898 | 7/1989 | Germany . |
| 04001614 | 4/1984 | Japan . |
| 01022804 | 7/1987 | Japan . |
| 07020856 | 12/1988 | Japan . |
| 2004775 | 8/1987 | Spain . |
| 2 211093 | 6/1989 | United Kingdom . |
| WO 95/17175 | 6/1995 | WIPO . |
| WO 9523009 | 8/1995 | WIPO . |
| 96 24329 A | 8/1996 | WIPO . |

OTHER PUBLICATIONS

Solids Stabilized Oil–in–Water Emulsion: Scavenging of emulsion droplets by fresh oil addition, Yan and Masilyah, *Colloids and Surfaces, A Physiochemical and Engineer Aspects*, 75 (1993) 123–132.

*Primary Examiner*—Jyothsna Venkat
*Attorney, Agent, or Firm*—Darryl C. Little; Tara M. Rosnell; George W. Allen

[57] ABSTRACT

The present invention relates to cosmetic applicators comprised of a sheet of porous or absorbent material which is impregnated with an oil-in-water emulsion composition. The oil-in-water emulsion compositions comprises an oil phase comprising from about 0.1% to about 5% by weight of the emulsion composition of an oil-soluble moisturizing agent, dispersed in an aqueous phase. The oil-soluble moisturizer has a mean particle size ranging from about 0.05 to about 7 microns. The oil-in-water emulsion comprises from about 0.1% to about 5% by weight of the emulsion of a surfactant and from about 0.05% to about 5% by weight of the emulsion of particulates. The viscosity of the oil-in-water emulsion composition ranges from about 1 to about 500 centipoise.

18 Claims, No Drawings

COSMETIC APPLICATORS WHICH CONTAIN STABLE OIL-IN-WATER EMULSIONS

TECHNICAL FIELD

The present invention relates to cosmetic applicators comprising absorbent sheets impregnated with stable oil-in-water emulsion compositions. The oil-in-water emulsion compositions contain particulates to provide stability to the emulsion composition. The stable oil-in-water emulsion compositions described herein can also be used by themselves (e.g., in a spray form) to provide an antibacterial benefit to skin.

BACKGROUND OF THE INVENTION

Consumers have in the past used absorbent sheets impregnated with topical compositions for a variety of purposes. For example, wipes impregnated with cleansing compositions are frequently used to conveniently wash hands and face while traveling or in public or anytime when water and soap are not readily accessible. However, the cleansing compositions impregnated into these wipes are often harsh to the skin or leave an undesirable sticky skin feel when applied to the skin. Consumers would prefer to use wipes which are not harsh or drying to the skin and which do not leave a sticky skin feel.

Wipes which provide a cleansing benefit, but which are not harsh or drying to the skin have been disclosed in the art. See, for example, EPA 613,675; Johnson & Johnson Consumer Products; Published Sep. 7, 1994 and WO 95/17175; The Procter & Gamble Company; Published Jun. 29, 1995, both of which disclose wipes which are impregnated with oil-in-water emulsion compositions.

Unfortunately, in order to impregnate a topical composition, including an oil-in-water emulsion composition, onto a wipe, and in order to ensure release of the oil from the wipe, the composition must have a water-thin viscosity. Oil-in-water emulsion compositions which are water-thin in viscosity are often very difficult to stabilize. As a result, when these water-thin oil-in-water emulsion compositions are impregnated onto a wipe, the emulsion may tend to separate. When the wipes are packaged together in a stack, the aqueous portion of the emulsion can sometimes sink to the bottom of the stack, while the oil portion of the emulsion stays on the top. This separation can be further accentuated by the wipe itself, which can act as a filter to accelerate phase separation of the emulsion.

It has now been found however, that water-thin oil-in-water emulsions which are suitably stable can be prepared by ensuring that the oil-soluble moisturizer comprising the oil phase of the emulsion has a particular mean particle size and by incorporating particulates into the emulsion composition. The particulates can be selected so that the emulsion compositions into which they are incorporated can provide an antibacterial benefit.

SUMMARY OF THE INVENTION

The present invention relates to cosmetic applicators comprised of a sheet of porous or absorbent material which is impregnated with a stable oil-in-water emulsion composition. The oil-in-water emulsion compositions comprise an oil phase comprising from about 0.1% to about 5.0% by weight of the emulsion composition of an oil-soluble moisturizer dispersed in an aqueous phase. The oil-soluble moisturizer has a mean particle size ranging from about 0.05 to about 7 microns. The oil-in-water emulsion compositions additionally comprise from about 0.1% to about 5% by weight of the emulsion composition of a surfactant and from about 0.05% to about 5% by weight of the emulsion composition of particulates. The viscosity of the oil-in-water emulsion composition ranges from about 1 to about 500 centipoise.

The present invention also relates to the stable oil-in-water compositions themselves.

DETAILED DESCRIPTION OF THE INVENTION

The present invention relates to cosmetic applicators comprised of a sheet of porous or absorbent material which is impregnated with a stable oil-in-water emulsion composition and to the stable oil-in-water compositions themselves.

The oil-in-water emulsion compositions comprise an oil phase comprising from about 0.1% to about 5% by weight of the emulsion composition of an oil-soluble moisturizing agent dispersed in an aqueous phase. The oil-soluble moisturizer has a mean particle size ranging from about 0.05 to about 7 microns. The oil-in-water emulsion compositions also comprise from about 0.1 to about 5% by weight of the emulsion composition of a surfactant and from about 0.05% to about 5% by weight of the emulsion composition of particulates. The viscosity of the oil-in-water emulsion composition ranges from about 1 to about 50 centipoise.

It has been found that oil-in-water emulsion which have a viscosity ranging from about 1 to about 500 centipoise, but which are suitably stable for impregnation onto an absorbent sheet can be prepared if the oil-soluble moisturizer comprising the oil phase of the emulsion has the hereinbefore described mean particle size and if particulates are incorporated into the emulsion composition at the levels hereinbefore described. The particulates can be selected so that the emulsion compositions into which they are incorporated can provide an antibacterial benefit. These stable oil-in-water compositions can also be used by themselves (e.g., as a lotion or a spray) to provide an antibacterial benefit to the skin.

The cosmetic applicators of the present inventions, including the materials used therein and processes for making, are described in detail as follows:

1. The Oil-in-Water Emulsion

The cosmetic applicators of the present invention are impregnated with a stable oil-in-water emulsion composition. The emulsion compositions suitable for use herein have a viscosity ranging from about 1 to about 500 centipoise, preferably from about I to about 300 centipoise, more preferably from about 1 to about 100 centipoise. Emulsion compositions which have a viscosity of greater than about 500 centipoise will be very difficult to impregnate into a variety of porous or absorbent sheets, and therefore, are not desirable for use herein. The oil-in-water emulsion compositions of the present invention typically have a pH ranging from about 2 to about 10. The oil-in-water emulsion compositions of the present invention are stable for at least 2 days at 120° F., preferably for at least 5 days at 120° F., more preferably for at least about 2 weeks at 120° F., and most preferably for at least 6 weeks at 120° F., as measured by the Stability Method set forth hereinafter in the Analytical Methods Section.

The oil phase of the oil-in-water compositions of the present invention comprises from about 0.1% to about 5%, preferably from about 0.2% to about 3%, more preferably from about 0.5% to about 2% by weight of the emulsion composition of an oil-soluble moisturizer. In general, the more oil-soluble moisturizer relative to the amount of surfactant (hereinafter described) that is present in the oil-in-water emulsions herein, the greater the improvement in stability that is provided by the present invention.

The oil-soluble moisturizer employed herein includes those commonly employed in cleansing creams and lotions, including, but not limited to, hydrocarbon oils and waxes such as mineral oil and petrolatum, vegetable and animal fats and oils, such as lanolin and its derivatives and vegetable oils and their derivatives, fatty acid and fatty alcohol esters, volatile and non-volatile silicones, and mixtures thereof. Other examples of oil-soluble moisturizers for use herein are described in 1 *Cosmetics, Science and Technology* 27–104 (M. Balsam and E. Sagarin, Ed; 1972), and U.S. Pat. No. 4,202,879, to Shelton, issued May 13, 1980, and U.S. Pat. No. 4,919,934; Deckner et al; Issued Apr. 24, 1990, all of which are herein incorporated by reference.

Volatile silicone oils useful herein are preferably cyclic. The following formula illustrates cyclic volatile polydimethylsiloxanes useful herein:

wherein n equals 3 to 7. Linear polydimethylsiloxanes contain from about 3 to about 9 silicone atoms per molecule and have the general formula:

wherein n equals 1 to 7. Linear volatile silicones materials generally have viscosities of less than about 5 centistokes at 25° C., while cyclic materials typically have viscosities of less than about 10 centistokes. A description of various volatile silicone oils is found in Todd et al, "Volatile Silicone Fluids for Cosmetics", *Cosmetics & Toiletries*, 91, pages 27–32 (1976), which is herein incorporated by reference.

Examples of volatile silicone oils include Dow Coming 344, Dow Coming 345, and Dow Coming 200 (manufactured by Dow Coming Corporation), Silicone 7207 and Silicone 7158 (manufactured by Union Carbide Corp.), SF 1202 (manufactured by General Electric), and SWS-03314 (manufactured by SWS Silicones, Inc.).

Non-volatile silicone oils useful as the oil-soluble moisturizer herein include polyalkylsiloxanes and polyalkylarylsiloxanes. The essentially non-volatile polyalkyl siloxanes useful herein include for example, polydimethyl siloxanes with viscosities of from about 5 to about 100,000 centistokes at 25° C. Such polyakyl siloxanes include the Vicasil series (sold by the General Electric Company) and the Dow Corning 200 series (sold by Dow Coming Corporation) Polyalkylaryl siloxanes include polymethylphenyl siloxanes having viscosities ranging from about 15 to about 65 centistokes at 25° C. These are available, for example, as SF 1075 methylphenyl fluid (sold by General Electric Company) and 556 Cosmetic Grade Fluid (sold by Dow Coming Corporation).

Non-polar fatty acid and fatty alcohol esters useful herein include, for example, ethyl hexyl palmitate, isodecyl neopentanoate, octadodecyl benzoate, diethyl hexyl maleate and PPG-2 mydrisyl ether propionate Hydrocarbons useful herein include isohexadecane (e.g., Permethyl 101 A supplied by Presperse), petrolatum and USP light (e.g., Klearol (®) or heavy (e.g., Kaydol ). Mineral oil is especially preferred for use herein.

The oil-soluble moisturizer employed in the emulsion compositions used in the present invention must have a mean particle size (e.g., diameter) ranging from about 0.05 to about 7 microns, preferably from about 0.05 microns to about 3 microns, more preferably from about 0.05 to about 2 microns. Oil-soluble moisturizers which do not have this particle size do not form emulsions having the requisite stability and, therefore, are not suitable for use herein.

The aqueous phase of the oil-in-water emulsion compositions used in the present invention comprises from about 90% to about 99%, preferably from about 92% to about 98%, more preferably from about 93% to about 96% by weight of the emulsion composition of water.

The oil-in-water emulsion compositions used in the present invention additionally comprise from about 0.05% to about 5%, preferably from about 0.05% to about 2%, more preferably from about 0.05% to about 1% by weight of the emulsion composition of particulates. Particulates useful for stabilizing the emulsion compositions employed in the present invention include 2,4,4'-trichloro-2'-hydroxy diphenylether (hereinafter "TCS" or "triclosan"); 3,4,4'-trichlorocarbanilide (hereinafter "TCC" or "triclocarban"), and zinc pyrithione (hereinafter "ZPT"). TCS, TCC and ZPT are especially preferred for use herein, since these particulates are antibacterial actives and, therefore, provide an antibacterial benefit as well as a stability benefit.

The oil-in-water emulsions used in the present invention also comprise from about 0.1% to about 5%, preferably from about 0.1% to about 2%, more preferably from about 0.1% to about 1% by weight of the emulsion of a surfactant or mixture of surfactants. A ratio of oil-soluble moisturizer to surfactant of at least about 0.75:1, preferably at least about 1:1 is especially preferred for use herein.

The surfactant can be a water-soluble surfactant or an oil-soluble surfactant, or both water-soluble surfactants and oil-soluble surfactants can be utilized. It is preferred that at least one oil-soluble surfactant be employed in the oil-in-water emulsions used in the present invention.

Suitable oil-soluble surfactants for use herein include, for example, nonionic surfactants such as ethoxylated alcohols, ethoxylated fatty esters, ethoxylated fatty oils, ethoxylated fatty acids, ethoxylated sorbitan esters, glycerol ester and ethoxylated alkyphenols and mixtures thereof.

Suitable water-soluble-surfactants for use herein include, for example, some of the non-ionic surfactants hereinbefore described, anionic surfactants such as sulfated surfactants, sulfonated surfactants, phosphated surfactants, carboxylated surfactants, sarcosinated surfactants, lactylated surfactants, and mixtures thereof, cationic surfactants, including amines and quaternary surfactants, and mixtures thereof, and amphoteric surfactants including imidazolines, lecithins, betaines and betaine derivatives, and mixtures thereof. Ammonium lauryl sulfate and ammonium laureth sulfate of anionic surfactants suitable for use herein.

The oil-in-water emulsions of the present invention also preferably contain from about 0.1% to about 2%, preferably from about 0.2% to about 1.5%, more preferably from about 0.5% to about 1% by weight of the emulsion composition of an organic solvent for the particulate. Suitable solvents for use herein include, for example, propylene glycol, dipropylene glycol, polyethylene glycol, polypropylene glycol, glycerol, 1,2,4-butanetriol, sorbitan esters, 1,2,6-hexanetriol, ethanol, isopropanol, butanediol, triethanolarnine, isopropyl myristate, benzyl alcohol, and mixtures thereof. In one embodiment of the present invention it is preferred that the oil-in-water emulsion composition be alcohol-free or substantially alcohol-free in order to eliminate drying effects. As used herein, the term "substantially alcohol-free" means that the emulsion composition contains less than about 2% by weight, preferably less than 1% by weight of the emulsion of alcohol. In this embodiment of the present invention, the organic solvent is preferably propylene glycol, dipropylene glycol, polypropylene glycol or glycerine.

The oil-in-water emulsion compositions employed in the present invention can also optionally contain a number of additional ingredients. These additional ingredients include various polymers for aiding the film-forming properties and substantivity of the emulsion composition, preservatives for maintaining the anti microbial integrity of the emulsion compositions, pH adjusters, water-soluble humectants, and antioxidants and agents suitable for aesthetic purposes such as fragrances, pigments and colorings.

The emulsion compositions used in the present invention are typically prepared by melting together the oil phase ingredients, including the oil-soluble moisturizer, the surfactants (both oil-soluble and water-soluble), any emulsifiers and the particulates, with stirring or shaking at temperatures ranging from about 20° C. to about 90° C. The aqueous phase (comprising water) is separately prepared at temperatures ranging from about 20° C. to about 90° C., and is then added with agitation to the oil phase. After a period of shaking or stirring with temperature maintained in the range of from about 20° C. to about 90° C., the preservatives and other ingredients are added.

I. The Porous or Absorbent Sheet

The finished emulsion is impregnated at the desired weight onto one or both sides of an absorbent sheet which may be formed from any woven or nonwoven fiber, fiber mixture or foam of sufficient wet strength and absorbency to hold an effective amount of the oil-in-water emulsion composition.

In particular, woven or nonwoven fabrics derived from "oriented" or carded fibrous webs composed of textile-length fibers, the major proportion of which are oriented predominantly in one direction are suitable for use herein. These fabrics can be in the form of, for example, wipes or towelettes (including baby wipes and the like) or also incorporated into feminine hygiene products such as sanitary napkins and the like.

Methods of making woven, nonwoven and cellulose cloths are not a part of this invention and, being well known in the art, are not described in detail herein. Generally, however, such cloths are made by air- or water-laying processes in which the fibers or filaments are first cut to desired lengths from long strands, passed into a water or air stream, and then deposited onto a screen through which the fiber-laden air or water is passed. The deposited fibers or filaments are then adhesively bonded together, and otherwise treated as desired to form the woven, nonwoven, or cellulose cloth.

Thermocarded nonwoven cloths (whether or not resin-containing) are made of polyesters, polyamides, or other thermoplastic fibers which can be spand bonded, i.e., the fibers are spun out onto a flat surface and bonded (melted) together by heat or chemical reactions.

The nonwoven cloth substrates used in the invention herein are generally adhesively bonded fibers or filamentous products having a web or carded fiber structure (when the fiber strength is suitable to allow carding) or comprising fibrous mats in which the fibers or filaments are distributed haphazardly or in random array (i.e., an array of fibers in a carded web where partial orientation of the fibers is frequently present, as well as a completely haphazard distributional orientation), or substantially aligned. The fibers or filaments can be natural (e.g., wool, silk, jute, hemp, cotton, linen, sisal, or ramie) or synthetic (e.g., rayon, cellulose ester, polyvinyl derivatives, polyolethins, polyamides, or polyesters) as have been described hereinabove. These nonwoven materials are generally described in Riedel "Nonwoven Bonding Methods and Materials", *Nonwoven World,* (1987).

The absorbent properties preferred herein are particularly easy to obtain with nonwoven cloths and are provided merely by building up the thickness of the cloth, i.e., by superimposing a plurality of carded webs or mats to a thickness adequate to obtain the necessary absorbent properties, or by allowing a sufficient thickness of the fibers to deposit on the screen. Any denier of the fiber (generally up to about 15 denier) can be used, inasmuch as it is the free space between each fiber that makes the thickness of the cloth directly related to the absorbent capacity of the cloth. Thus, any thickness necessary to obtain the required absorbent capacity can be used.

III. Preparation of the Absorbent Sheets Impregnated with Oil-in Water Emulsion Composition Any method suitable for the application of aqueous or aqueous/alcoholic impregnates, including flood coating, spray coating or metered dosing, can be used to impregnate the fibrous webs herein with the emulsion compositions described herein. More specialized techniques, such as Meyer Rod, floating knife or doctor blade, which are typically used to impregnate water-in-oil emulsion into absorbent sheets may also be used.

The emulsion should preferably comprise from about 100% to about 400%, preferably from about 200% to about 400% by weight of the absorbent sheet.

After coating, the applicators may be folded into stacks and packaged in any of the moisture and vapor impermeable packages known in the art.

ANALYTICAL METHODS

A variety of parameters used to characterize elements of the present invention are quantified by particular experimental analytical procedures. Each of these procedures is described in detail as follows:

1. Method to Measure Viscosity of Oil-in-Water Emulsion

A digital Brookfield viscometer Model DV II with spinde 41 is used to measure the viscosities of the oil-in-water emulsions used herein. The operating speed of the viscometer is set at I RPM. An oil-in-water emulsion sample is placed in a 2 ml cup. The cup is placed in the viscometer and an analysis is performed for 3 minutes. The viscosity of the oil-in-water emulsion is then read and recorded.

2. Method to Measure Stability of Emulsion

The stability of the oil-in-water emulsion used in the present invention is measured by visual observation of the samples for creaming, phase separation or precipitation of matter over time under ambient and high temperature (120° F.) conditions. A sample is stable if it exhibits no creaming, phase separation or precipitation at 120° F. for at least 1 day, preferably at least 5 days.

3. Method to Measure Droplet Size of Oil-Soluble Moisturizer

The mean droplet (e.g. particle) size of the oil-soluble moisturizer is measured by phase contrast microscopy, using appropriate lenses for magnification (~800–1000X) with a Zeiss microscope.

EXAMPLES

The following are nonlimiting Examples of the oil-in-water emulsion-containing cosmetic applicators of the present invention.

A. Four oil-in-water emulsion compositions are prepared according to Table I below.

Compositions 1 and 2 represent the stable oil-in-water emulsion compositions of the present invention. Compositions 3 and 4 represent oil-in-water emulsion compositions which do not contain particulates (e.g., TCS). Compositions 3 and 4 are not stable.

TABLE I

|  | 1 | 2 | 3 | 4 |
|---|---|---|---|---|
| Mineral Oil | 2.00 | 1.00 | 2.00 | 1.00 |
| Steareth-20 | 0.55 | 0.55 | 0.55 | 0.55 |
| Steareth-2 | 0.45 | 0.45 | 0.45 | 0.45 |
| Propylene Glycol | 1.00 | 1.00 | 1.00 | 1.00 |
| Triclosan | 0.15 | 0.15 | 0.00 | 0.00 |
| Other minor ingredients | 0.36 | 0.36 | 0.36 | 0.36 |
| Water | 95.49 | 96.49 | 95.64 | 96.64 |
| pH of emulsion | 6.0 | 5.9 | 6.0 | 5.9 |
| viscosity of emulsion (cp) | <500 | <500 | <500 | <500 |
| Mean particle size of oil-soluble moisturizer (microns) | 0.05–1 | 0.05–1 | 1–2 | 1–2 |
| Stability of emulsion (at 120° F.) | >5 days | >5 days | <5 days | <5 days |

B. Compositions 1–4 are impregnated onto absorbent sheets as follows:

Composition 1 is impregnated onto a wet and air laid woven absorbent sheet comprised of 85% cellulose and 15% polyester at 260% by weight of the absorbent sheet by pouring the composition onto the sheet via a cup.

What is claimed is:

1. A cosmetic applicator comprising a porous or absorbent sheet impregnated with an oil-in-water emulsion composition, wherein, the oil-in-water emulsion composition comprises:
   A. an oil phase comprising from about 0.1% to about 5% by weight of the emulsion of an oil-soluble moisturizer where in the oil-soluble moisturizer is mineral oil wherein the oil-soluble moisturizer has a mean particle size ranging from about 0.05 to about 7 microns; and
   B. an aqueous phase;
   wherein the oil-in-water emulsion composition comprises from about 0.1% to about 5% by weight of the emulsion composition of a surfactant and from about 0.05% to about 5% by weight of the emulsion composition of a particulate where in the particulate is selected from the group consisting of triclosan, triclocarban and zinc pyridine, and wherein the oil-in-water emulsion composition has a viscosity in the range of from about 1 to about 500 centipoise.

2. The cosmetic applicator of claim 1 wherein the surfactant within the oil-in-water emulsion comprises an oil-soluble surfactant.

3. The cosmetic applicator of claim 1 wherein the oil-in-water emulsion composition is stable for at least 5 days at 120° F.

4. The cosmetic applicator of claim 3 wherein the oil-in-water emulsion comprises from about 90% to about 99% water.

5. The cosmetic applicator of claim 4 wherein the oil-soluble moisturizer within the oil-in-water emulsion is present at a level of from about 0.2% to about 3% by weight of the emulsion composition.

6. The cosmetic applicator of claim 5 wherein the particulate within the oil-in-water emulsion is present at a level ranging from about 0.05% to about 2% by weight of the emulsion composition.

7. The cosmetic applicator of claim 6 wherein the oil-in-water emulsion composition additionally contains a preservative.

8. The cosmetic applicator of claim 7 wherein the oil-in-water emulsion composition additionally comprises an organic solvent.

9. The cosmetic applicator of claim 8 wherein the oil-in-water emulsion composition is substantially alcohol-free.

10. The cosmetic applicator of claim 9 wherein the level of surfactant within the oil-in-water emulsion composition ranges from about 0.1 to about 2% by weight of the emulsion composition.

11. The cosmetic applicator of claim 10 wherein the ratio of oil-soluble moisturizer to surfactant within the oil-in-water emulsion composition is at least about 0,75:1.

12. The cosmetic applicator of claim 11 wherein the oil-in-water emulsion composition has a viscosity ranging from about 1 to about 300 centipoise.

13. The cosmetic applicator of claim 1 wherein the emulsion composition comprises from about 100% to about 400% by weight of the porous or absorbent sheet.

14. An oil-in-water emulsion composition comprising:
   A. an oil phase comprising from about 0.1% to about 5% by weight of the emulsion of an oil-soluble moisturizer wherein in the oil-soluble moiturizer is mineral oil, wherein the oil-soluble moisturizer has a mean particle size ranging from about 0.5 to about 7 microns; and
   B. an aqueous phase;
   wherein the oil-in-water emulsion composition comprises from about 0.1% to about 5% by weight of the emulsion composition of a surfactant and from about 0. 1% to about 5% by weight of the emulsion composition of a particlate where in the particulate is selected from the group consisting of triclosan, triclocarban and zinc pyridine, and wherein the oil-in-water emulsion composition has a viscosity in the range of from about 1 to about 100 centipoise.

15. The oil-in-water emulsion composition of claim 14 wherein the surfactant within the oil-in-water emulsion comprises an oil-soluble surfactant.

16. The oil-in-water emulsion composition of claim 15 which is stable for at least 5 days at 120° F.

17. The oil-in-water emulsion composition of claim 16 wherein the oil-in-water emulsion composition additionally comprises an organic solvent.

18. The oil-in-water emulsion composition of claim 17 wherein the oil-in-water emulsion composition is substantially alcohol-free.

* * * * *